United States Patent [19]

Bridges et al.

[11] Patent Number: 5,624,420
[45] Date of Patent: Apr. 29, 1997

[54] DISPOSABLE TRAINING PANTS HAVING A NON-PERFORATED TEAR LINE THROUGH ELASTIC

[75] Inventors: Russell P. Bridges, Cincinnati; James R. Golan, Ginti; Stephen J. Lange, Cincinnati; Michael J. Madill, Wyoming; Robert H. Siegfried, Cincinnati, all of Ohio

[73] Assignee: The Procter & Gamble Company, Cincinnati, Ohio

[21] Appl. No.: 503,330

[22] Filed: Jul. 17, 1995

Related U.S. Application Data

[63] Continuation of Ser. No. 83,069, Jun. 25, 1993, abandoned.
[51] Int. Cl.$^6$ .............. A61F 13/15; A41B 9/00; B29C 65/06; B32B 31/20
[52] U.S. Cl. .............. 604/365; 604/366; 604/385.2; 604/396; 2/401; 156/73.5; 156/290; 156/308.4
[58] Field of Search .............. 604/385.1, 385.2, 604/392, 393, 394, 396, 366, 365; 156/73.5, 290, 308.4; 2/400–406

[56] References Cited

U.S. PATENT DOCUMENTS

| | | |
|---|---|---|
| 3,563,822 | 2/1971 | Fesh . |
| 4,205,679 | 6/1980 | Repke et al. .............. 604/394 |
| 4,280,230 | 7/1981 | LaFleur . |
| 4,581,772 | 4/1986 | Smith . |
| 4,610,680 | 9/1986 | LaFleur . |
| 4,619,649 | 10/1986 | Roberts . |
| 4,641,381 | 2/1987 | Heran et al. .............. 604/392 |
| 4,646,362 | 3/1987 | Heran et al. .............. 604/392 |
| 4,671,793 | 6/1987 | Hults et al. . |
| 4,735,622 | 4/1988 | Acuff et al. . |
| 4,743,239 | 5/1988 | Cole . |
| 4,747,846 | 5/1988 | Boland et al. .............. 604/385.2 |
| 4,854,984 | 8/1989 | Ball et al. . |
| 4,909,804 | 3/1990 | Douglas, Sr. . |
| 4,919,738 | 4/1990 | Ball et al. . |
| 5,074,854 | 12/1991 | Davis . |
| 5,163,932 | 11/1992 | Nomura et al. .............. 604/396 |
| 5,236,430 | 8/1993 | Bridges .............. 604/396 |

FOREIGN PATENT DOCUMENTS

2267024  11/1993  United Kingdom .............. 604/396

Primary Examiner—Robert A. Clarke
Assistant Examiner—K. M. Reichle
Attorney, Agent, or Firm—Dinsmore & Shohl

[57] ABSTRACT

Non-perforated tear lines for removal and evacuation of contents of disposable undergarments such as training pants. Non-perforated tear lines include a series of bond sites which are shaped, sized, spaced and arranged to provide a zone of weakness to permit severance of nonelasticized portions as well as elastic disposed in the waistband, the body of the pant, and the elastic leg bands for complete removal. Bond sites are formed by displacing a portion of material such that a thickened outer edge defines a weakened area of reduced thickness. Thus, elastic in the waistband may be disposed continuously 360 degrees around the wearer's waist, and elastic in the leg bands may be disposed continuously 360 degrees around the wearer's legs. In addition, improved pants having elasticized ear flaps in the body of the pants can be conveniently removed from the wearer. The shape, size, spacing and arrangement of the individual bond sites is determined for each material used in order to permit severance of the particular material while preventing premature removal. Because the tear lines of this invention are capable of separating elastic, location of the tear lines is not limited to side seams, but may be placed on the front of the pants for convenience.

11 Claims, 10 Drawing Sheets

DISPOSABLE TRAINING PANTS HAVING A NON-PERFORATED TEAR LINE THROUGH ELASTIC

This is a continuation of U.S. patent application Ser. No. 08/083,069, filed Jun. 25, 1993, now abandoned.

FIELD OF THE INVENTION

The present invention relates generally to disposable undergarments which may be opened quickly and conveniently to facilitate evacuation of contents and removal from the wearer. Examples of such undergarments include disposable diapers, disposable training pants, disposable undergarments for incontinent adults and the like. The present invention relates more particularly to disposable undergarments having tear lines comprising individual bond sites which are capable of severing elastic waistbands, elastic leg bands and elastic in the pants chassis so that the elastic waistband and leg bands may be continuous, and elastic may be disposed throughout the pants chassis for improved fit.

BACKGROUND OF THE INVENTION

Young children and incontinent adults wear disposable undergarments to absorb and contain bodily exudates. Toilet training is the process by which a child makes the transition from wearing diapers to wearing underwear. During the toilet training process, the child learns to control his or her bodily functions so that the child may relieve itself in a toilet rather than soiling an undergarment. Training pants are primarily used to facilitate toilet training by acquainting the child with an undergarment that is distinguishable from diapers and similar to underwear so that the child will associate controlling its bodily functions with wearing the new undergarment. Not only are disposable training pants less bulky than disposable diapers, but the manner of dressing and undressing, i.e., inserting the wearer's legs in the leg openings and sliding the pants onto the lower torso and doing the reverse to remove them, is identical to underwear. Thus, the child becomes accustomed to taking down and pulling up the training pants in order to use the toilet.

Accidents are, however, inevitable during the toilet training process; therefore, it is essential that training pants can be quickly and easily removed. In this way, disposable training pants are similar to disposable diapers because the pants may be opened and removed from the child without pulling the child's legs through the pants which could, and often does, result in smearing excrement or urine on the child. Once removed, disposable training pants are discarded; disposable training pants are not designed to be laundered or reused.

Because children are different sizes, and toilet training takes place at different ages, the training pants must fit bodies in a range of sizes. In addition, incontinent adults use disposable undergarments. Manufacturers of training pants have had to use several different sets Of manufacturing equipment to produce the range of sizes necessary; however, an improved training pant that fits a broader range of sizes has been developed by Hasse, et. al. in U.S. patent application Ser. No. 795,560 and is incorporated by reference herein. The Hasse disposable training pant has at least two elasticized ear flaps in the body of the garment to accommodate various sized wearers. It is, therefore, desirable to have a means for opening the pants to quickly and easily remove the soiled pants. Until now, an opening means capable of severing elastic was not available.

Most prior art discloses separable side seams for removal of disposable training pants. Other mechanisms employed for removal of training pants includes breakaway panels and tear strands.

There are several general disadvantages to employing a separable side seam method of panty removal. The primary disadvantage is that the seams must be capable of easy and convenient separation, and yet, the seams must have sufficient strength to prevent premature opening during use. Side seams, particularly at the waistband and leg bands, are subject to the most strain during use; therefore, it would be advantageous to construct the side seams with the single purpose of providing sufficient strength to prevent premature opening. In order to have this single purpose for the side seams, the tear line or separation point for the pants needs to be located somewhere other than at the side seam. The requirement of easy and convenient separation at the side seams automatically limits the amount of strength that may be imparted to the side seam. In addition, tear lines at the side seams require the child to turn to each side in order for the caretaker to grasp the pants with sufficient strength and torque to tear the pants. It would be advantageous to have an opening method that allows the pants to be opened towards the front rather than at the sides.

Known methods of separation at the side seams of disposable training pants include perforation or scoring of the side seam so that either the seam itself fails or the material adjacent to the seam fails when torn. Chain stitching has also been used for separable side seams such that when an end of the stitching is pulled, the seam unravels and the seam separates. An additional method of opening is to insert a breakaway panel in between two seams at one or both of the sides where the breakaway panel is constructed of a weaker material so that this material gives way before the side seam does. Generally, the seaming area disclosed in the prior art is void of any waistband or leg band to avoid interfering with the separability of the pants. A method of removal capable of separating elastic would permit training pants to have continuous elastic bands in the waist and legs providing improved fit and comfort.

The improved training pants disclosed by Hasse in U.S. patent application Ser. No. 795,560, shows an elasticized disposable training pant with a high degree of stretch such that the disposable training pants will comfortably fit wearers in a broad range of sizes. The disposable training pants having at least two, and preferably four, elasticized ear flaps having an elastomeric member secured thereto to form a laminate; and mechanically stretching the laminate so that the ear flap is permanently elongated and the laminate is elastically extensible in the direction of initial stretching, once the initial stretching forces are removed from the laminate.

Accordingly, a disposable training pant is provided having either continuous or non-continuous elastic in the waistband and leg bands, elastic disposed in the pants chassis for facilitating an improved fit for a wider range of sizes, and an opening means that is capable of separating the elastic members therein.

It is an object of the present invention to provide disposable training pants having an improved means of opening the training pants to facilitate removal from the wearer.

It is another object of the present invention to provide disposable training pants which have non-perforated tear lines that can tear through elastic disposed in the waistband, the leg band or pants chassis.

It is a further object of the present invention to provide disposable training pants having non-perforated tear lines which can be imposed on the front of the training pant.

It is still another object of the present invention to provide disposable training pants which are simple and economical to produce.

It is yet another object of the present invention to provide a disposable training pant having a non-perforated tear line comprising individual bond sites sized, shaped, spaced and arranged such that the tear line has sufficient strength during regular use to prevent premature separation of the pant from the wearer.

It is yet a further object of the present invention to provide a disposable training pant having a non-perforated tear line comprising individual bond sites sized, shaped, spaced and arranged such that the tear line is capable of severing elasticized material, elasticized waist and leg bands and several layers of pants material and elastic members.

It is still a further object of the present invention to provide a disposable training pant having markers to guide the caretaker to the proper starting point for tearing or for visually enhancing the training pants.

It is still another object of the present invention to provide disposable training pants having a non-perforated tear line which does not require positioning at the side seams of the training pants.

It is still a further object of the present invention to provide disposable training pants having the appearance and feel of cloth underwear rather than the appearance and feel of a diaper.

SUMMARY OF THE INVENTION

Accordingly, disposable training pants are provided having at least two layers, an absorbent member, elastic leg bands, an elastic waistband, and elastic disposed in ear flaps in the pants chassis to accommodate wearers of different sizes. The present invention has non-perforated tear lines that separate disposable undergarments including elasticized portions to facilitate evacuation of contents and easy removal of soiled pants.

Although the present invention discloses non-perforated tear lines disposed on a non-elasticized training pant and two elasticized alternative embodiments, it should be understood that these tear lines could be used on any disposable undergarment. One of the elasticized alternative embodiments of the present invention has the non-perforated tear lines disposed upon the Hasse pant disclosed in U.S. patent application Ser. No. 795,560. The second elasticized alternative embodiment is a modification of the Hasse pant having a continuous elastic waistband and continuous elastic leg bands through which non-perforated tear lines may extend.

To provide quick and convenient removal of soiled training pants, non-perforated tear lines can be placed at one or more places on the pants extending through the waistband, the pants body and a leg band. The tear line of the present invention is designed to open when an adult grasps on opposing sides of the tear line at the waist with two hands and pulls apart. The tear begins at the elasticized waistband, progresses through the pants chassis, and concludes through one of the elasticized leg bands thereby providing total separation of the pant through the tear line. The tear lines can be placed anywhere between the side seams and the absorbent assembly on either the front or back of the pants. If the tear lines are located near the side seams, the caretaker generally can not tear at both places without turning the child or changing hand positions. In addition, the side seams may be constructed with maximum strength if the tear line is located other than at the side seams.

The tear line is created by fusing material in the pants with a series of bond sites shaped, sized, spaced and arranged geometrically to provide a desired line of weakness extending from the waistband through the pants chassis and leg bands. Size, shape, spacing and arrangement of bond sites is very material specific. A balance must be maintained between providing bonds sites sufficiently close together to allow tearing along the weakened zone, and yet, bond sites must be spaced far enough apart so that the garment has sufficient residual strength. If elastic strands are used to elasticize the waistband, leg bands or chassis, overlapping bond sites are used so that each strand is severed. Overlapping bond sites insure that every elastic strand is cut regardless of its position, and leaves sufficient material between bonds for girth strength. Through non-elasticized portions or elasticized portions containing elastic film instead of elastic strands overlapping bond sites may be used, but generally are not necessary. Unlike perforations, the bond sites are not holes in the material, but are thinned and resolidified membranes. Thus, the present non-perforated tear line is a weakened zone that has more strength than a perforated tear line, and will be less likely to rupture prematurely during use.

The number of layers of the chassis may vary along the length of the tear line. One or more of the layers may be a polymeric, such as polyethylene, which melts at a different point than the primary strength polymeric.

The above will become more apparent to those skilled in the art after a consideration of the following detailed description taken together with the accompanying drawings in which a preferred embodiment of the invention is described.

DETAILED DESCRIPTION OF THE PREFERRED EMBODIMENT

The tear lines of the present invention are described as being used on particular embodiments of a disposable training pant. However, it should be understood that the present invention is intended for use on other training pant designs as well as on other types of disposable undergarments which may include incontinent briefs, disposable diapers, and the like.

As used herein, the term "disposable training pants" refers to disposable undergarments which absorb and contain body exudates and more specifically refers to disposable undergarments which comprise an absorbent means therein and are intended to be worn by a child while the child is being trained to control bladder and bowel movements and to use the toilet.

Figure 1:
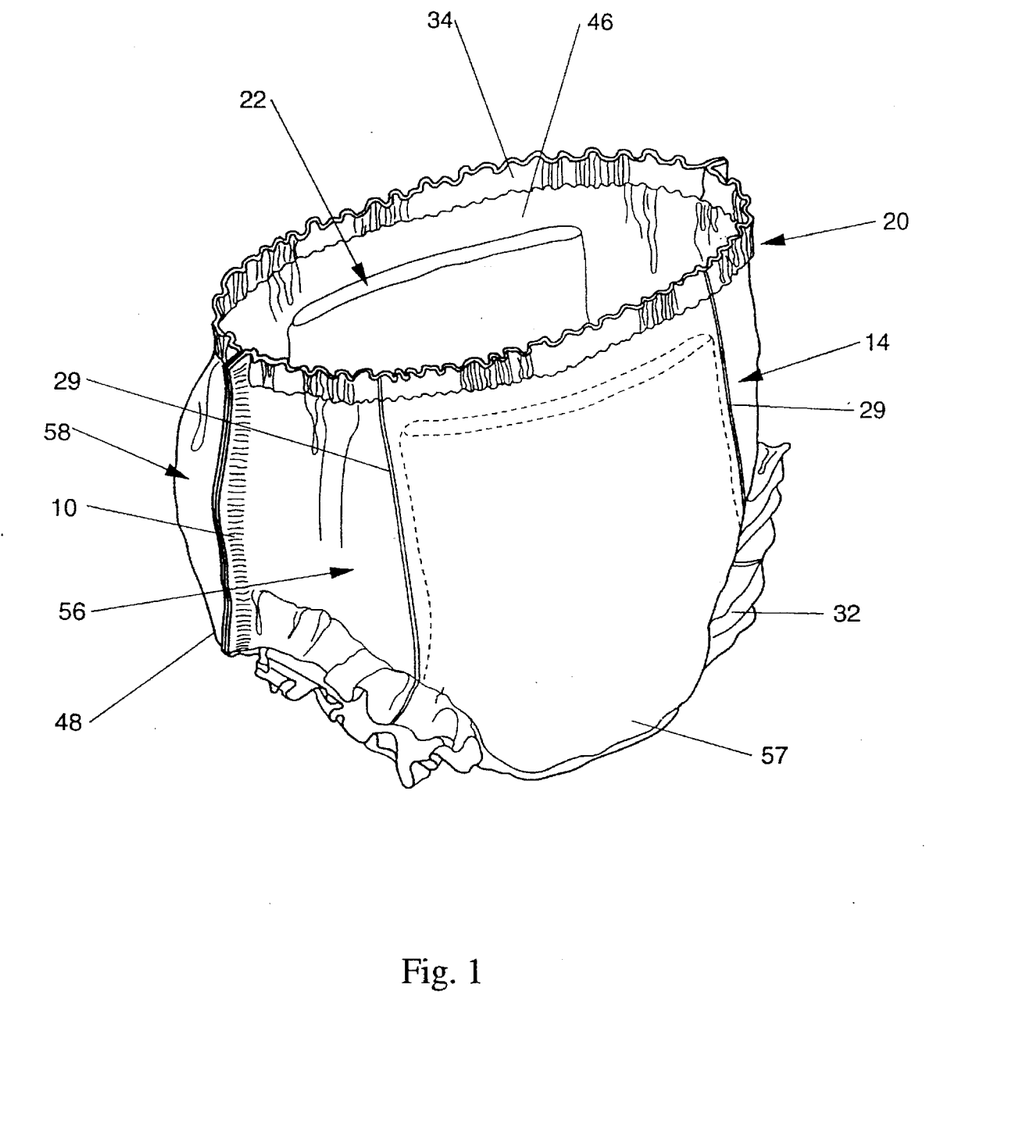
FIG. 1 is a perspective view of a basic training pant showing the tear lines.

Referring now to the drawings in detail wherein like reference numerals represent like elements throughout the figures, FIG. 1 is a perspective view of the present invention in a basic training pant, reference numeral 20 refers generally to the training pants. The training pants 20 have a front portion 56 and a rear portion 58 that are joined through a contiguous crotch portion 57. The front portion 56, rear portion 58 and the crotch portion 57 together comprise the chassis 14 of the pants 20. The front portion 56 and the rear portion 58 are joined at side seams 10 such that a waist opening and two leg openings are formed. The tear lines 29 are each disposed on the front portion 56, and extend continuously on the right side from right leg opening to the waist opening, and on the left side from left leg opening to the waist opening. The chassis 14 comprises an outer layer 48 secured to an inner layer 46 and an absorbent assembly 22 attached to the inner layer 46.

The waistband of the disposable training pants is the portion of the training pants which is adjacent to the wearer's waist. The outer layer 48 and the inner layer 46 are joined together to form waistband 34 and may contain an elastic band disposed in a portion of the waistband 34, or throughout the entire waistband 34. Since elastic will not interfere with or hinder the tearing ability of the non-perforated tear lines, the disposable training pants of the present invention may be constructed with an elasticized waistband entirely surrounding the waist of the wearer. Elasticized waistbands described in the prior art disclose preferred embodiments having elastic only through a portion of the waistband due to the adverse effects of the elastic on the opening method of the pants.

Leg bands 32 are the portion of the training pants 20 surrounding the leg openings for fitting closely around the legs of the wearer to preclude leaking from the pants down the wearer's legs. Elasticized leg bands 32 accommodate various leg sizes, and afford a better fit. The outer layer 48 and the inner layer 46 are joined together to form leg bands 32 and may contain either an elastic band disposed in a portion of the leg bands (usually in the crotch portion), or throughout the entire leg bands 32. Since elastic will not interfere with or hinder the tearing ability of the non-perforated tear lines, the disposable training pants of the present invention may be constructed with elasticized leg bands completely surrounding the legs of the wearer. The prior art teaches that it is preferable to have elastic disposed in only a portion of the leg bands, usually the crotch portion, so that the elastic will not interfere with the separability of the pants. However, due to the ability of the present invention to tear through elastic, a preferred embodiment of the present invention that is discussed in detail herein below, discloses elastic throughout the entire length of the leg bands to facilitate a closer fit around the wearer's legs for enhanced leakage prevention.

As shown in FIG. 1, the disposable training pant 20 has on the front portion 56, two continuous non-perforated tear lines 29 extending from each leg opening, right leg opening and left leg opening, to the waist opening. The tear lines 29 permit the training pants 20 to be easily removed from the wearer by grasping at the waistband on opposing sides of one of the tear lines 29 and pulling apart along the tear line 29, and then repeating along the other tear line 29. The training pant 20 opens between the waist opening and the right leg opening on the right side of the training pant 20, and between the waist opening and the left leg opening on the left side of the training pant 20. The preferred location of the tear lines is such that they are disposed in the shortest line from the point on the leg band that would contact the top of the wearer's thigh to the waistband.

A tear line 29 is a zone of weakness created by fusing a series of individual bond sites into the waistband 34, chassis 14 and the leg band 32 of the training pants 20. The size, shape, spacing and arrangement of bond sites depends on the type of material being bonded, and may vary within the same tear line. The bond sites may be almost any geometric configuration (i.e. ovoid, circular, elliptical, rectangular, capsular, triangular, etc.), but the preferred shape of the bond site for this invention is ovoid, circular or capsular. A balance must be achieved between sufficiently weakening the material to permit tearing, against sufficiently spacing the bond sites so that the material retains sufficient strength to prevent premature opening. This balance must be determined for the exact materials being bonded together; however, those skilled in the art could readily select suitable materials as well as determine shape, size, spacing and arrangement of the bond sites.

Figure 1A:
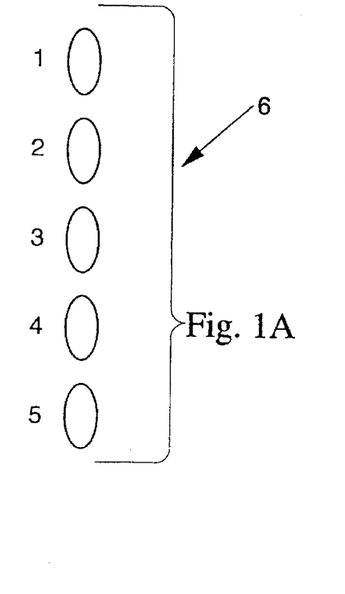
FIG. 1A is a schematic representation depicting the relative positions of five bond sites as the bond sites would be aligned to form a tear line.
Figure 1B:
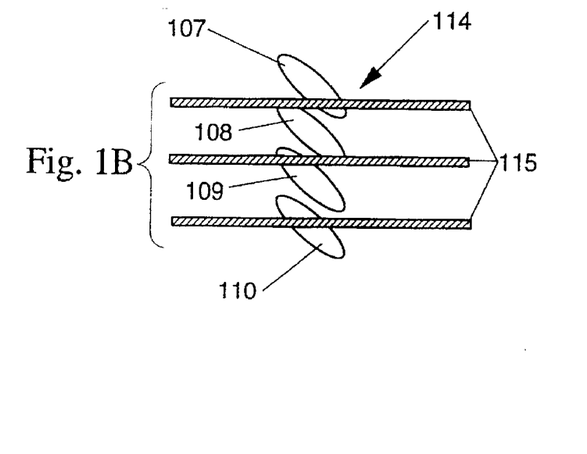
FIG. 1B is a close up view of the tear line through the elastic waistband of FIG. 1.

The non-perforated tear line is capable of separating either elastic film or elastic strands; however, separating portions of the pants having elastic strands requires overlapping bond sites 107–110 collectively referred to as 114 as shown in FIG. 1B. FIG. 1B illustrates how the overlapping oval bonds 114 cut every elastic strand 105 regardless of its position and leaves unbonded material between bonds for girth strength. While the overlapping arrangement 114 in the elastic bands 105 permits rupture of the elastic strands, it does not destroy the function of the elastic band in that overall, the band retains its elastic extensibility for maximum comfort and fit. Adjacent bond sites (e.g. 107, 108) are overlapped in a horizontal plane and a vertical plane, but they do not contact each other. Use of overlapping bond site arrangements is not limited to portions containing elastic strands, but may be used in nonelasticized portions or in elasticized portions containing elastic film.

FIG. 1A shows a portion of a tear line 29 through a portion of the training pant chassis 14 that does not require overlapping of the bond sites 6. The bond sites 6 shown in FIG. 1A are spaced sufficiently close together so that the material is sufficiently weakened to permit that specific material to tear progressively along the tear line 29. However, the bond sites 6 are sufficiently spaced apart so as to retain sufficient residual strength of the unbonded fabric that premature opening of the tear line will not occur.

Figure 1C:
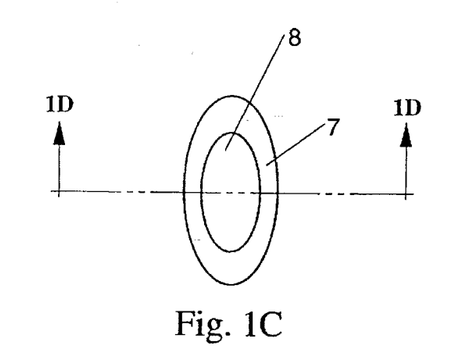
FIG. 1C is a schematic representation depicting bond site 5 of FIG. 1A.
Figure 1D:
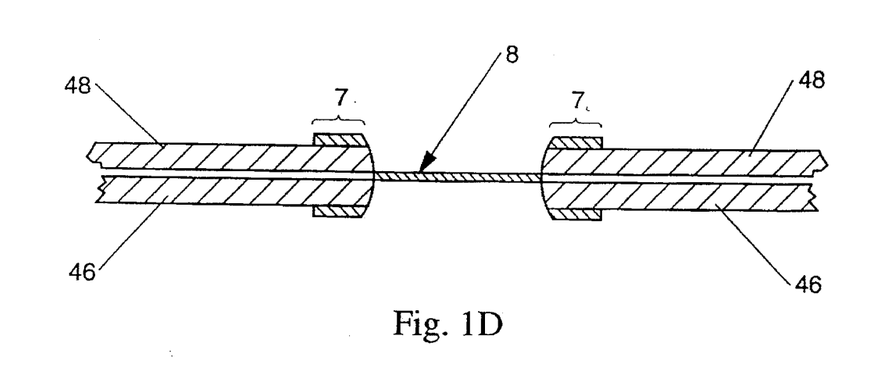
FIG. 1D is a sectional view through the training pants of FIG. 1 taken through a bond site as schematically represented by the sectional line 1D—1D in FIG. 1C.

The bond sites may be created by either ultrasonic bonding or rotary pressure bonding. Both processes impart high energy to a particular point of the polymeric material layers of the pant which causes the material to soften and flow; 50% to 90% of chassis material at this point is displaced to a thickened outer edge. As shown in FIG. 1C and FIG. 1D, when the material resolidifies it resembles a window or an area of reduced thickness 8 defined by a thickened outer edge of fused material 7. The thickened outer edge 7 of the bond site is thicker than the layers of adjacent, unbonded material 46, 48. As shown in FIG. 1D, approximately 50-90% of the fabric is displaced from the inner portion 8 to the circumference or outer edge 7 of the bond site, leaving approximately 10-50% of the fabric in an area of reduced thickness 8 or window. The end result is a bond site as shown in FIG. 1C that resembles an oval donut except that the donut does not have a hole, but has a thin layer of material 8 surrounded by a thickened outer edge 7 of fused material. The area of reduced thickness 8 is the melted and resolidified material in bond site 5, whereas the thickened outer edge 8 is melted and resolidified material that was pushed out of the region of high mechanical pressure 7.

Figure 1E:
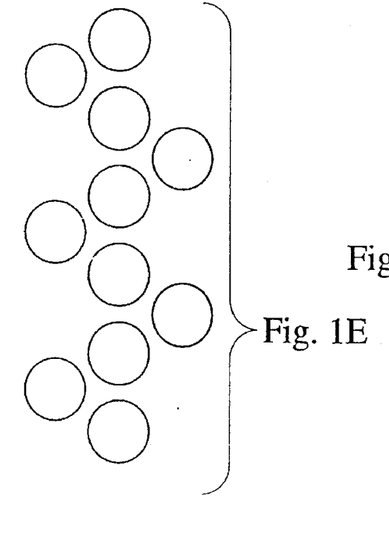
FIG. 1E is a close up of an alternate tear line.
Figure 1F:
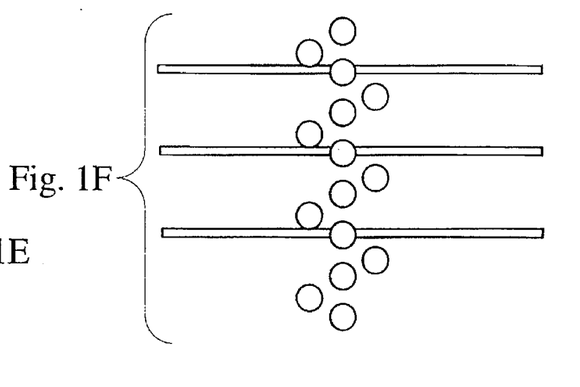
FIG. 1F is a close up view of the tear line of FIG. 1E as it would look in the waistband of FIG. 1.
Figure 1G:
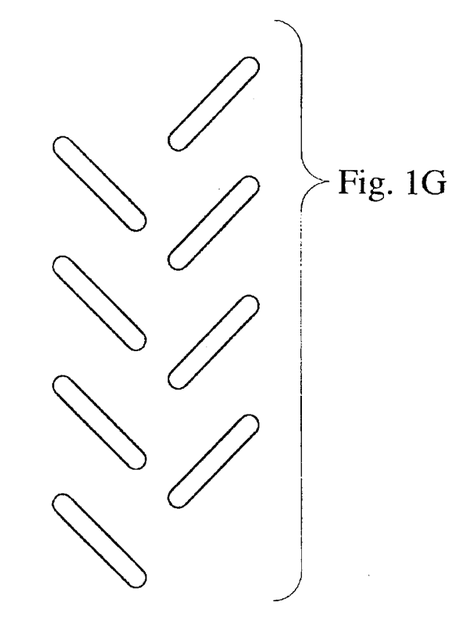
FIG. 1G is a close up view of an alternate tear line.
Figure 1H:
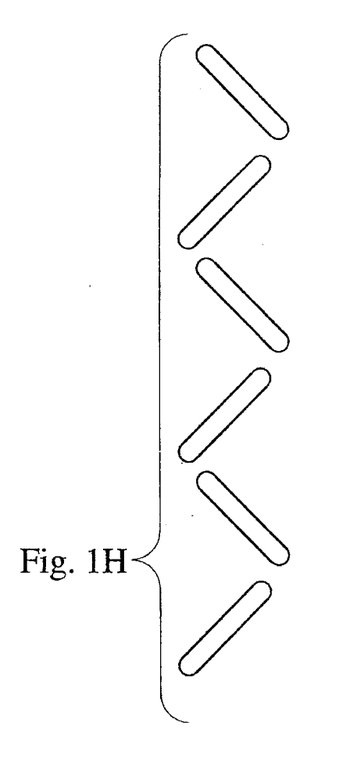
FIG. 1H is a close up view of another alternate tear line.
Figure 2:
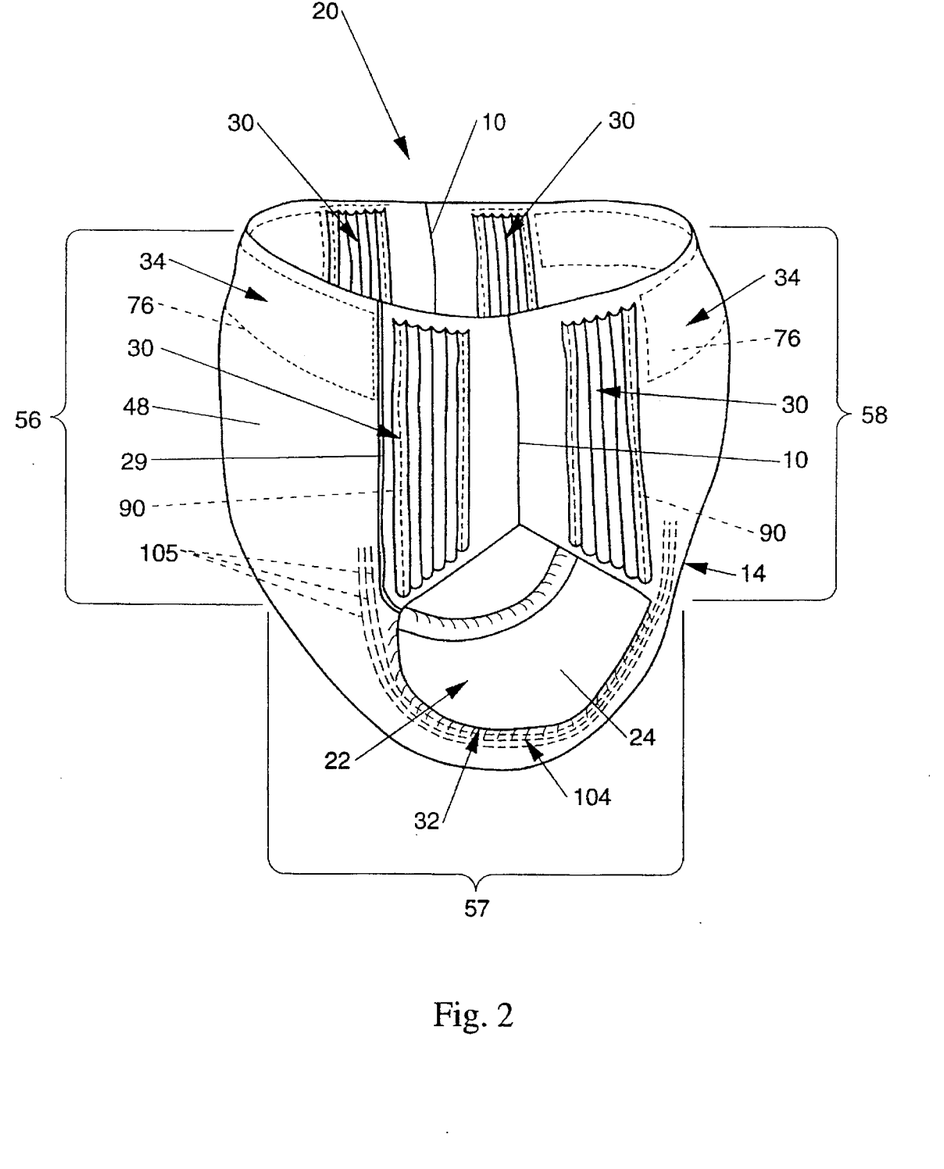
FIG. 2 is a preferred embodiment of the training pants having elastic in portions of the waistband and leg bands, and elasticized ear flaps.
Figure 7:
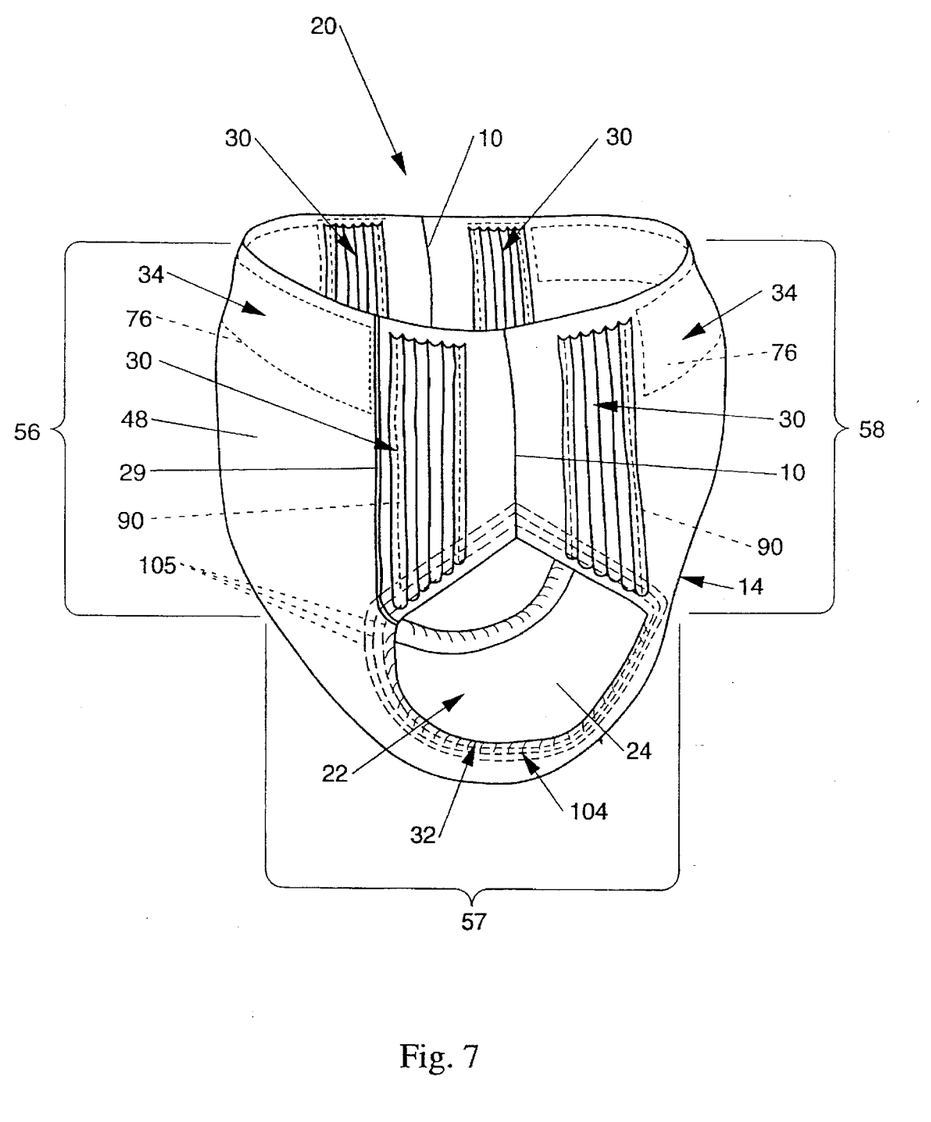
FIG. 7 is a perspective view of a preferred embodiment of the training pants having elastic continuously disposed in the waistband and leg bands.

The tear lines 29 are located, as shown by FIG. 1, FIG. 2 and FIG. 7, preferably on the front portion 56 to facilitate easy removal by the caretaker. Non-perforated tear lines 29 can be placed anywhere between the side seams 10 and the absorbent assembly 22 on the training pants 20, such as on the rear portion 58 near the center, or on either the rear portion 58 or the front portion 56 in the vicinity of the side seams 10, so long as each tear line 29 extends continuously between a leg opening and the waist opening. FIG. 1, FIG. 2, and FIG. 7 show the preferred shape of the tear lines 29, although the shape of the tear lines 29 may be straight or curved or any combination thereof. The orientation of the tear line 29 to machine direction of the product may be parallel or perpendicular or anything in between. Therefore, the geometric shape and arrangement of the bond sites are unlimited so long as each tear line 29 extends continuously between the waist opening and one of the leg openings. Furthermore, additional bond sites (not shown) may be disposed on the training pant 20 to guide the caretaker to the starting points of the tear lines 29, or to enhance the attractiveness of the pant. Those skilled in the art can readily select suitable materials for constructing the training pants, and use bond sites that are shaped, sized, spaced and arranged so that they will sever the pants, yet retain sufficient girth strength. A preferable tear line comprises a herring bone pattern of capsular bond sites as shown in FIG. 1G. A preferred alternative tear line comprises a zigzag pattern of capsular bond sites as shown in FIG. 1H. In addition, FIG. 1E and FIG. 1F show a zigzag pattern of circular bond sites. Each circular bond site has a diameter of 0.05 of an inch. Adjacent bond sites are spaced 0.01 from one another edge-to-edge for ensuring sufficient girth strength in the training pants.

The preferred embodiment shown in FIG. 2 superposes the tear lines of the present invention on the training pant of U.S. patent application Ser. No. 795,560 by Hasse. An alternative preferred embodiment of the present invention, as shown in FIG. 7 and discussed in detail herein below, discloses the tear lines of the present invention on a modification of the Hasse training pant. The training pants 20 shown in both FIG. 2 and FIG. 7 comprise a chassis 14, side seams 10, an absorbent assembly 22, and tear lines 29.

Figure 3:
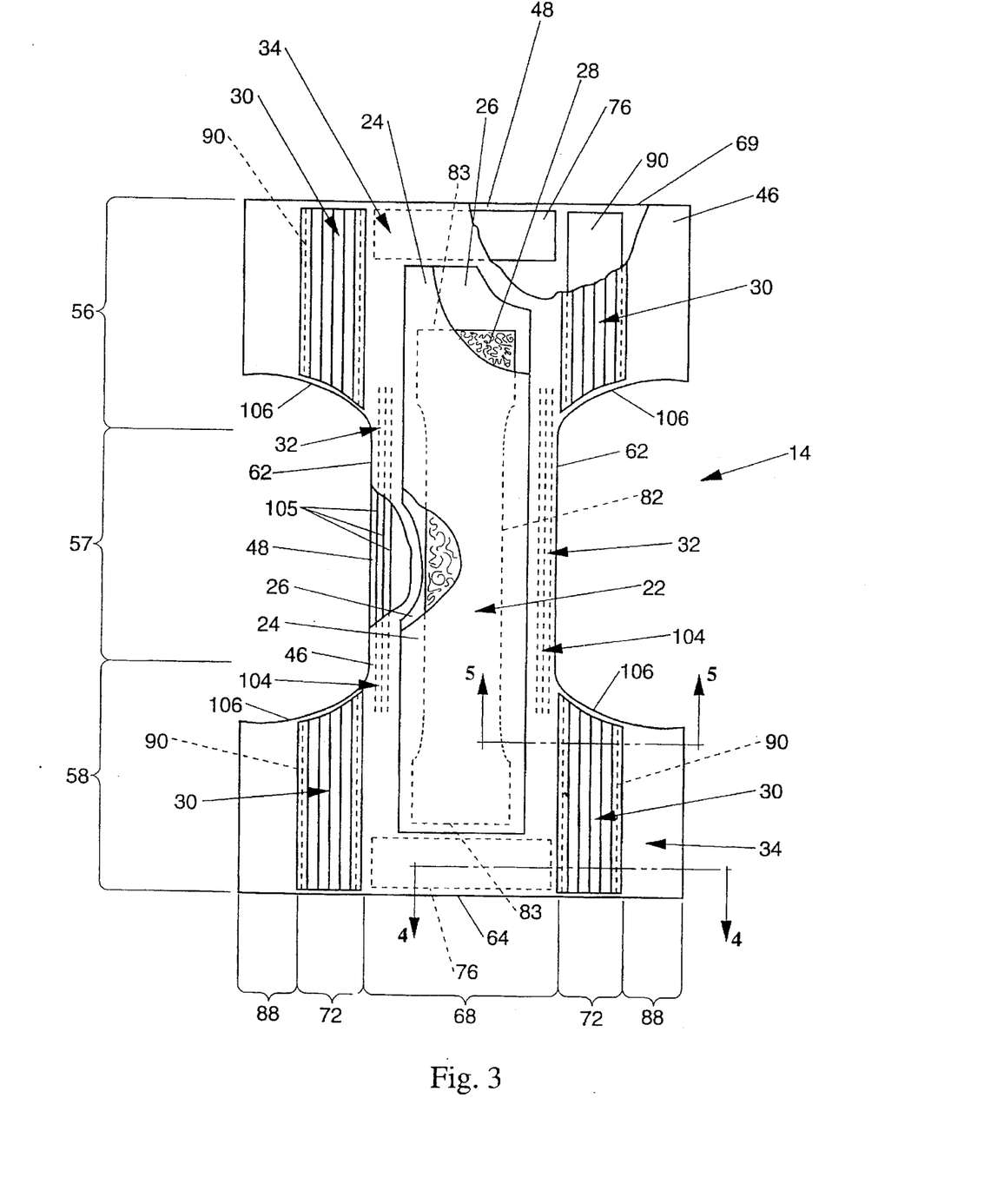
FIG. 3 is a plan view of the laid out training pants of FIG. 2 having portions cut away to reveal the underlying structure.

FIG. 3 is a partially cut-away plan view of the disposable training pants 20 of FIG. 2, prior to the front portion 56 and the rear portion 58 of the chassis 14 being joined together by the seams 10. The chassis 14 of the present invention preferably has a modified hourglass shape. The chassis 14 will have at least a front portion 56, a rear portion 58, a contiguous crotch portion 57, longitudinal side regions 88, and ear flaps 72. The ear flaps 72 will comprise an elastic ear flap member 90 operatively associated with each ear flap 72 to form a laminated ear flap which will be elastically activated by a mechanical stretching process which will be described in greater detail herein below. The absorbent assembly 22 is secured to the chassis 14 in the crotch portion 57.

As shown in FIG. 2 and FIG. 3, front portion 56 and rear portion 58 are contiguous through the crotch portion 57. Front portion 56 and rear portion 58 are joined together at side seams 10 such that a waist opening and two leg openings are formed. On each side of the pants, in the longitudinal side regions 88, side seams 10 extend uninterruptedly from each leg opening to the waist opening. Preferably, each of the tear lines 29 are disposed on the front portion 56 of the chassis 14, and are continuous from each leg opening to the waist opening.

As shown in FIG. 3, a preferred embodiment of the chassis 14 further comprises an outer layer 48 and an inner layer 46 with the elastic ear flap members 90, elastic waistband members 76 and elastic strands 105 (this figure shows elastic strands to demonstrate overlapping bondsite arrangements, but elastic film could be used instead) preferably secured between the inner layer 46 and outer layer 48. The outer layer 48 is that portion of the chassis 14 which will form the exterior of the disposable training pants 20. The outer layer 48 is compliant, soft feeling, and non-irritating to the wearer's skin. A suitable outer layer may be manufactured from a wide range of materials, such as plastic films; or woven or non-woven webs of natural fibers (e.g. wood or cotton fibers), synthetic fibers (e.g. polyester or polypropylene fibers), synthetic fibers (e.g. polyester or polypropylene fibers), or a combination of natural and synthetic fibers. Preferably, the outer layer 48 is hydrophobic and is made of a material containing a significant amount of thermoplastic fibers, typically 50% or more preferably, 100%. Preferably the outer layer is a nonwoven web of polypropylene or polyethylene fibers. A suitable outer layer is Series 6700 Nonwovens manufactured by Scott Nonwovens of Landisville, N.J.

The inner layer 46 is that portion of the chassis 14 which will form the interior of the chassis 14, and will contact at least the waist and legs of the wearer. The inner layer is also compliant, soft feeling, and non-irritating to the wearer's skin. A suitable inner layer 46 may be manufactured from a wide range of materials, such as plastic films; or woven or non-woven webs of natural fibers (e.g. wood or cotton fibers), synthetic fibers (e.g. polyester or polypropylene fibers), or a combination of natural and synthetic fibers. Preferably the inner layer 46 is made of the same material as the outer layer 48. A suitable inner layer is Series 6700 Nonwovens manufactured by Scott Nonwovens of Landisville, N.J.

The inner layer 46 is preferably positioned adjacent to the outer layer 48 and is preferably joined thereto by attachment means (not shown) such as those well known in the art. For example, the inner layer 46 may be secured to the outer layer 48 by a uniform continuous layer of adhesive, a patterned layer of adhesive, or an array of separate lines, spirals, or spots of adhesive. Adhesives which have been found to be satisfactory are manufactured by Findley adhesives of Elm Grove, Wis. and marketed as Findley 2031. Alternatively, the attachment means may comprise heat bonds, pressure bonds, ultrasonic bonds, dynamic mechanical bonds, or any other suitable attachment means or combinations of these attachment means as are known in the art. In a preferred embodiment of the present invention, the inner layer 46 and the outer layer 48 are indirectly joined together by directly joining them to the elastic ear flap members 90, elastic waistband members 76, and elastic strands 105 and are joined directly to each other in the areas extending beyond the elastic ear flap members 90, elastic waistband members 76, and elastic strands 105.

In a preferred embodiment of the present invention, at least a portion of the chassis inner and outer layers 46, 48 will be subjected to mechanical stretching in order to provide a "zero strain" stretch laminate that forms the elasticized ear flaps 30.

Elasticized leg bands 32 are the portions of the chassis 14 surrounding the leg openings for fitting closely around the wearer's legs to preclude leaking from the pants. Each elasticized leg band 32 may comprise several different embodiments for reducing the leakage of body exudates in the leg regions, however, it is preferred that each elasticized leg band 32 comprise at least a side flap 104 and one or more elastic strands 105 or elastic film (not shown).

The waistband 34 of the chassis 14 is the portion of the training pants 20 which is adjacent to the wearer's waist. The chassis 14 of the disposable training pants 20 preferably comprises an elasticized waistband 34 disposed adjacent the end edge 64 of the disposable training pants 20 in at least the rear portion 58, and more preferably has an elastic band 34 disposed in both the front portion 56 and the rear portion 58 adjacent rear end edge 64 and front edge 69. While the elasticized waistband 34 can comprise a separate element affixed to the chassis 14 of the disposable training pants 20, the waistband is preferably an extension of other elements of the disposable training pants 20 such as the inner layer 46, the outer layer 48, or any combination of these elements and an elastomeric material joined thereto to form an elasticized waistband. Disposable training pants are often constructed so as to have two elasticized waistbands; one positioned in the front portion 56 and one positioned in the rear portion 58. This embodiment of the disposable training pants 20 at least has an elasticized waistband 34 disposed in at least the central region 68 of the rear portion 58. Preferably, as shown in FIG. 2 and FIG. 3, another elasticized waistband is disposed in the front portion 56. Preferably both elasticized waistbands 34 are disposed between the elasticized ear flaps 30.

The elasticized waistband 34 may be constructed in a number of different configurations including those described herein with regard to the elasticized side panels. In a preferred embodiment of the present invention shown in FIG. 4, the elasticized waistband 34 comprises an elastic band 76 interposed between the inner cover 46 and the outer cover 48 and operatively associated with either or both the inner cover 46 and the outer cover 48 to gather the front portion 56 and rear portion 58 of the disposable training pants 20.

Figure 4:
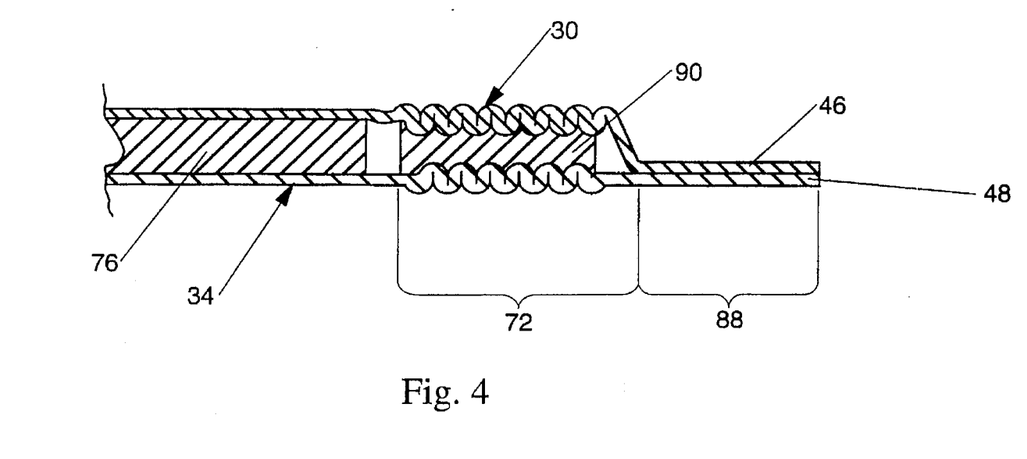
FIG. 4 is a fragmentary sectional view of the chassis shown in FIG. 3 taken along sectional line 4—4 thereof.

Any suitable elastomeric material as known in the art may be used as the elastic band 76 of the present invention. Examples of suitable elastomeric materials include elastomeric films; formed elastic scrim; elastomeric films such as heat shrinkable elastic materials; elastomeric film laminates such as a laminate of a heat-shrinkable elastomeric film and a resilient member; elastomeric stretch laminates such as "zero strain" stretch laminates as described hereinafter or mechanically stretched pretensioned stretch laminates; and elastic strands made from rubber, "LYCRA", or other materials. In a preferred embodiment, the elastic band 76 comprises a heat shrinkable elastomeric film. A suitable elastomeric film is "EXXTRAFLEX" film by Exxon.

In a preferred embodiment, the chassis 14 comprises elasticized ear flaps 30 in the front portion 56 and the rear portion 58. The elasticized ear flaps 30 are unitary elements of the chassis, i.e. they are not separately manipulative elements secured to the chassis, but rather are formed from and are extensions of the chassis materials. The elasticized ear flaps 30 provide an elastically extensible feature that provides a more comfortable and contouring fit by initially conformably fitting the disposable garment to the wearer and sustaining this fit throughout the time of wear well past when the disposable garment has been loaded with exudates since the elasticized ear flaps allow the sides of the disposable garment to expand and contract.

As shown in FIG. 3, each ear flap 72 comprises that portion of the chassis 14 that extends laterally outwardly from and along the central region 68 of the chassis 14 to the longitudinal side region 88 of the chassis 14. The ear flap 72 generally extends longitudinally from the end edge 64 of the chassis 14 to the portions of the longitudinal edge 62 of the chassis 14 that forms the leg opening (this segment of the longitudinal edge 62 being designated as leg edge 106). In a preferred embodiment of the present invention, each ear flap 72 is formed by the portions of the inner layer 46 and the outer layer 48 that extend beyond the central region 68 of the chassis 14.

In a preferred embodiment of the present invention, the elastic ear flap members 90 are operatively associated with the chassis 14 in the ear flaps 72, preferably between the inner layer 46 and the outer layer 48, so that the elastic ear flap members 90 allow the elasticized ear flaps 30 to be elastically extensible in the lateral direction (laterally elastically extensible.) As used herein, the term "elastically extensible" means a segment or portion of the chassis that will elongate in at least one direction (preferably the lateral direction for the ear flaps and the waistbands) when tensional forces (typically lateral tensional forces for the ear flaps and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof.

The elastic ear flap members 90 can be joined to either the inner layer 46, outer layer 48, or both using either an intermittent bonding configuration or a substantially continuous bonding configuration. As used herein, an "intermittently" bonded laminate web means a laminate web wherein the plies are initially bonded to one another at discrete spaced apart points or a laminate web wherein the plies are substantially unbonded to one another in discrete spaced apart areas. Conversely, a "substantially continuously" bonded laminate web means a laminate web wherein the plies are initially bonded substantially continuously to one another throughout the areas of interface.

In a preferred embodiment of the present invention, the elastic ear flap member 90 is substantially continuously bonded to both the inner layer 46 and the outer layer 48 using an adhesive. A glue applicator may be used to apply a substantially uniform and continuous layer of adhesive to either the outer layer 48, the inner layer 46, or both in those predetermined areas where the substantially untensioned elastic ear flap member 90 will be placed. In a particularly preferred embodiment, the adhesive selected is stretchable and the glue applicator comprises a spiral pattern applicating system.

Alternatively, the elastic ear flap member 90 and any other components comprising the "zero strain" portions of the disposable training pants 20 may be intermittently or continuously bonded to one another using unheated adhesive, heat bonding, pressure bonding, ultrasonic bonding, dynamic mechanical bonding, or any other method as is known in the art.

The elastic ear flap members 90 may take on a number of different sizes, shapes, configurations and materials. For example, the elasticized ear flaps 30 may be formed from one or a plurality of elastic ear flap members 90 operatively associated in each ear flap 72; the elastic ear flap members may have varying widths and lengths; or the elastic ear flap members may comprise relatively narrow strands of elastomeric material or a larger area elastomeric patch. Suitable elastomeric materials for use as the elastic ear flap members 90 include "live" synthetic or natural rubber, elastomeric films (including heat shrinkable elastomeric films), elastomeric scrim, elastomeric woven or nonwoven webs, elastomeric composites such as elastomeric nonwoven laminates, or the like. One elastomeric material which has been found to be especially suitable for use as the elastic ear flap member 90 is Exxon's "EXXTRAFLEX" film.

As shown in FIG. 2, the elastic ear flap member 90 comprises a patch of elastomeric material (elastomeric patch) that preferably extends through the entire length of the ear flap 72 in the front and rear portions 56, 58. Thus, the elastic ear flap member 90 preferably extends from the end edge 64 of the chassis 14 inward to the leg edge 106 of the ear flap 72. The length and width of the elastic ear flap members 90 are dictated by the disposable garment's functional design. Thus, while the elastic ear flap member 90 preferably extends through the entire length of the ear flap 72, the elastic ear flap member 90 may extend through only a portion of the length of the ear flap 72.

In a preferred embodiment of the chassis as shown in FIG. 3, the longitudinal side region 88 is that portion of the chassis 14 that extends laterally outwardly from the ear flap 72 to the longitudinal edge 62 of the chassis 14. The longitudinal side region 88 generally extends longitudinally from the end edge 64 of the chassis 14 to the portion of the longitudinal edge 62 of the chassis 14 that forms the leg opening (this segment of the longitudinal edge 62 being designated as leg edge 106). While the longitudinal side region 88 can comprise a separate element affixed to the ear flap 72 of the chassis 14, the longitudinal side region is preferably an extension of other elements of the chassis 14 such as the inner layer 46, the outer layer 48, the topsheet 24 or the backsheet 26 or any combination of these elements. In a preferred embodiment of the present invention each longitudinal side region 88 is formed by portions of the inner layer 46 and outer layer 48 that extend beyond the ear flap 72.

Referring again to FIG. 2, seams 10 are preferably formed by bonding together the longitudinal side regions 88 of the front portion 56 with the longitudinal side regions 88 of the rear portion 58. The seam 10 can be formed in a number of different ways. For example, the seam 10 can be formed by bonding together portions of outwardly extending longitudinal side regions 88 to form an outwardly extending fin seam, bonding together portions of inwardly extending longitudinal side regions 88 to form an inwardly extending fin seam, the longitudinal side regions 88 may be overlapped and bonded together, or the longitudinal side regions 88 may be bonded together using any other seam configurations that are well known in the art. The bonding can be by any suitable means well known in the art appropriate for the specific material employed in the longitudinal side region 88 of the chassis 14; thus sonic sealing, heat sealing, adhesive bonding, sewing, and the like may be appropriate techniques.

Figure 6:
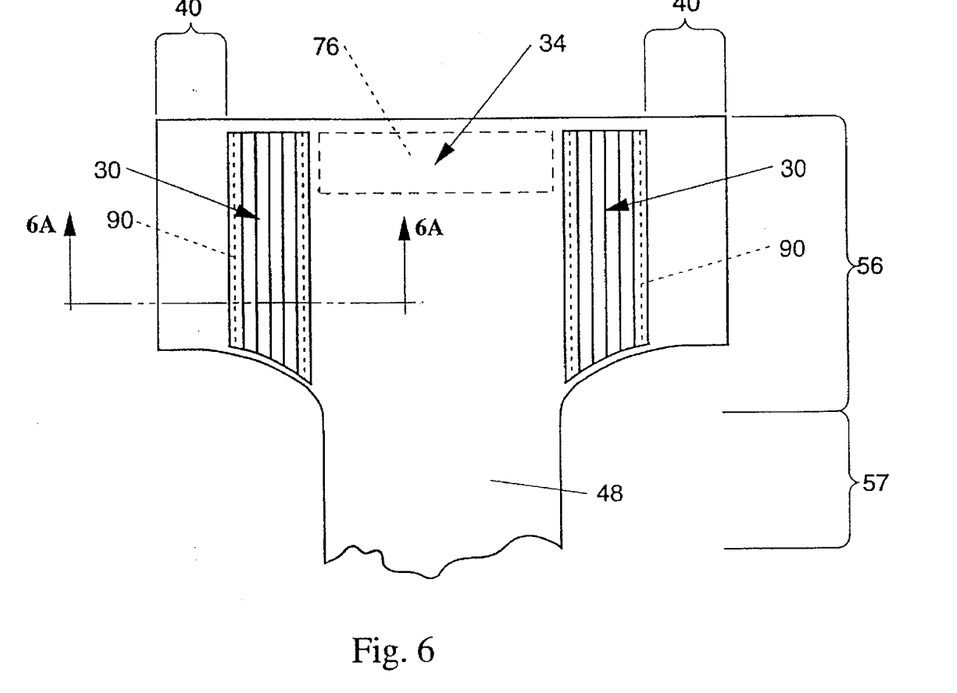
FIG. 6 is a fragmentary plan view of the chassis of FIG. 3, having been folded in the crotch portion such that the front portion and rear portion are overlapped.
Figure 6A:
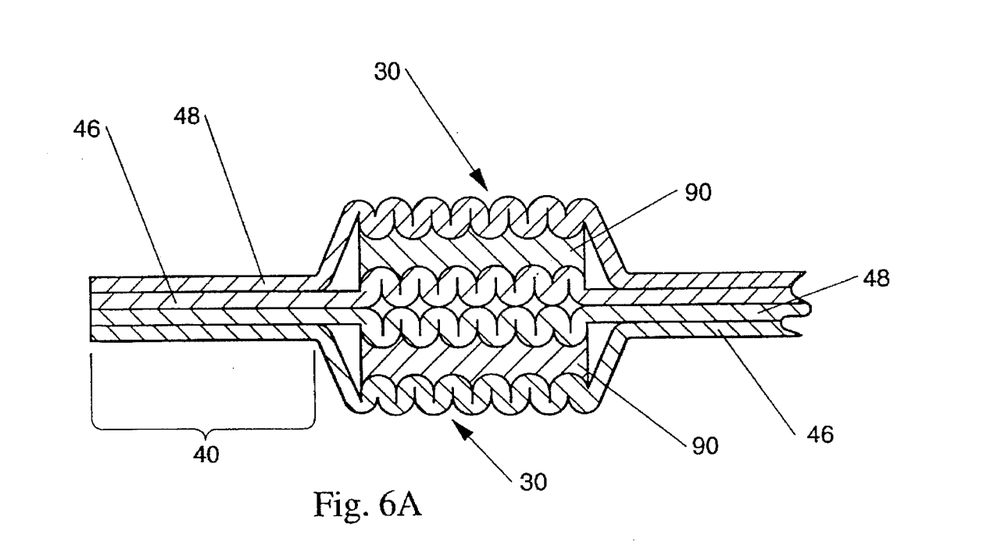
FIG. 6A is a fragmentary sectional view of the folded chassis shown in FIG. 6 taken along section line 6A—6A of FIG. 6.

In a preferred embodiment of the present invention, the disposable undergarment is formed by folding the chassis in the crotch portion 57 so that the longitudinal side regions 88 of the front portion 56 are substantially superposed with the longitudinal side regions 88 of the rear portion 58, as shown in FIG. 6, forming two seaming areas 40. FIG. 6A shows a preferred embodiment of the seaming area 40 comprising the longitudinal side region 88 of the front portion 56 and the longitudinal side region 88 of the rear portion 58. Preferably, the layers of material making-up the seaming area, have similar melting points. More preferably, each layer of the seaming area is made of the same material. In a preferred embodiment, each layer of the seaming area 40 will comprise 100% polypropylene fibers.

The seam 10 is preferably formed by treating the seaming area 40 with mechanical energy sufficient to cut a portion of the seaming area 40 while simultaneously fusing a narrow marginal area adjacent to the cut. The fused marginal area is a relatively small region and provides a finished flangeless seam. As used herein the term "flangeless seam" refers to a seam which extends from the disposable training pants 20 about 1/16" or less. Preferably the flangeless seam will extend from the garment about 1/32" or less. In a preferred embodiment, the flangeless seam is substantially a splice between the front portion 56 and rear portion 58 of the chassis 14. As used herein, the term "splice" refers to the act or result of joining end to end two pieces of sheet material to form a continuous length such that the thickness of the joint is no greater or not much greater than the thickness of the sheet materials.

As used herein, the term "mechanical energy" will be used to refer to mechanical energy (e.g., the energy employed in ultrasonic bonding or autogeneous pressure bonding) as well as to thermal energy (e.g., the energy employed in heat sealing). Preferably, ultrasonic energy is used to simultaneously cut and bond the seaming area 40 to produce the seams 10 of the present invention. Preferably, the mechanical energy is input to the seaming area 40 using an ultrasonic apparatus.

The training pants 20 will also comprise an absorbent assembly 22. The absorbent assembly 22 of the disposable training pants 20 is an insert, i.e. an element formed separately from the chassis and inserted therein. The absorbent assembly 22 is any absorbent means which is generally compressible, conformable, non-irritating to the wearer's skin, and capable of absorbing and retaining liquids such as urine and other certain body exudates.

Figure 5:
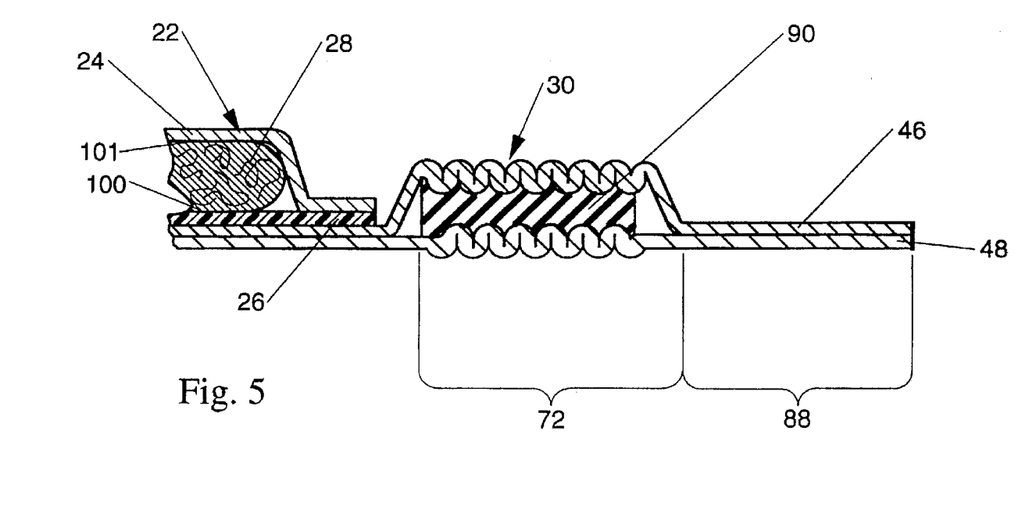
FIG. 5 is a fragmentary sectional view of the chassis shown in FIG. 3 taken along section line 5—5.

As shown in FIG. 5, the absorbent assembly 22 of the disposable training pants 20 preferably comprises an absorbent core 28 and an outer covering layer comprising a topsheet 24 and a backsheet 26. The absorbent assembly 22 is preferably positioned adjacent the inner layer 46 and is preferably joined thereto by attachment means (not shown) such as those well known in the art. Suitable attachment means are described hereinbelow with respect to joining the backsheet 26 to the absorbent core 28.

The absorbent core 28 may be any absorbent means which is generally compressible, conformable, non-irritating to the wearer's skin, and capable of absorbing and retaining liquids such as urine and other certain body exudates. As shown in FIG. 3 and FIG. 5, the absorbent core 28 has a garment surface 100, a body surface 101, side edges 82 and end edges 83.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding, meltblown polymers including coform, cross-linked cellulosic fibers, tissue including tissue wraps, absorbent foams, absorbent sponges, superabsorbent polymers, absorbent gelling materials, or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the disposable training pants 20. Further, the size and absorbent capacity of the absorbent core 28 may be varied to accommodate wearers ranging from infants through adults.

A preferred embodiment of the absorbent assembly 22 has a modified hour-glass shape absorbent core 28. While a preferred embodiment of the absorbent assembly 22 has a modified hourglass-shaped absorbent core 28, it should be understood that the size, shape, configuration and total absorbent capacity of the absorbent core 28 may be varied to accommodate wearers ranging from infants to adults. Therefore, the dimensions, shape and configuration of the absorbent core may be varied (e.g., the absorbent core may have a varying caliper, or a hydrophilic gradient, or may or may not contain absorbent gelling materials). The absorbent core 28 is preferably a batt of airfelt and particles of absorbent gelling material, about 13 centimeters wide (lateral dimension), about 37 centimeters long (longitudinal dimension) and approximately 8 centimeters across the narrowest part of the crotch portion 57. Preferably, the portion of the absorbent core that will be generally located in the front portion 56 and crotch portion 57 will have a higher basis weight than the portion of the absorbent core that will be generally located in the rear portion 58. More preferably, the portion of the absorbent core that will be generally located in the front portion 56 and crotch portion 57 will have a basis weight three times the basis weight of the portion of the absorbent core that will be generally located in the rear portion 58. In a preferred embodiment of the absorbent core 28, about 25.4 centimeters of the absorbent core's length will be generally located in the front portion 56 and crotch portion 57 and will have a basis weight of about 0.69 grams per square inch, and 11.4 centimeters of the absorbent core's length will be generally located in the rear portion 58 and will have a basis weight of about 0.23 grams per square inch.

The backsheet 26 is positioned adjacent the garment surface 100 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola and Tucker on Mar. 4, 1986, and which is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g. urine) and is preferably manufactured from a thin plastic film, although other flexible liquid impervious materials may also be used. As used herein, the term flexible refers to materials which are compliant and will readily conform to the general shape and contours of the human body. The backsheet 26 prevents the exudates absorbed and contained in the absorbent core 28 from wetting articles which contact the disposable training pants 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet is a film having a thickness of from about 0.012 mm (0.5 mil) to about 0.051 mm (2.0 mils).

The size of the backsheet 26 is dictated by the size of the absorbent core 28 and the exact disposable garment design selected. In a preferred embodiment, the backsheet 26 will wrap around at least the absorbent core and possibly over the edge portions of the topsheet 24 in at least the crotch portion 57, so that the elasticized leg cuff 32 will be free from any backsheet material, and, thus, are not inhibited by the backsheet material. Alternatively, the topsheet 24 may wrap around the core and under the edge portions of the backsheet 26 in at least the crotch portion 57, or the topsheet 24 and backsheet 26 may be "side-notched" in the crotch portion 57 so that the elasticized leg cuffs 32 are not inhibited by the backsheet material.

The topsheet 24 is positioned adjacent the body surface 101 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 is compliant, soft feeling, and non-irritating to the wearer's skin. Further, the topsheet 24 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 24 is made of hydrophilic material comprising about 20% to 30% rayon so as to feel wet and signal a discharge of urine to a toilet training child.

There are a number of manufacturing techniques which may be used to manufacture the topsheet 24. For example, the topsheet 24 may be a nonwoven web of fibers. When the topsheet comprises a nonwoven web, the web may be spunbonded, carded, wet-laid, meltblown, hydroentangled, combinations of the above, or the like. A preferred topsheet is carded and thermally bonded by means well known to those skilled in the fabrics art. Preferably, the topsheet 24 is made of a hydrophilic material comprising about 20% to about 35% rayon so as to feel wet and signal a discharge of urine to a toilet training child. A suitable topsheet is manufactured by Fiberweb North America and available as 80/20 polypropylene/rayon carded thermally bonded nonwoven.

While in a preferred embodiment of the present invention, the topsheet 24 does not form a part of the chassis 14, but is separately manufactured and inserted as part of the absorbent assembly 22 onto the chassis, the chassis 14 may be made without an inner layer 46, and the topsheet 24 of the absorbent assembly 22 may extend beyond the edges of the backsheet 26 in at least the front and rear portions 56, 58 of the chassis 14 such that the topsheet 24 will be disposed over the elastic ear flap members 90 and form the inner surface of the chassis 14 (shown as FIG. 10 in the Hasse application). In this embodiment, at least a portion of the topsheet 24 is subjected to mechanical stretching in order to provide a "zero strain" stretch laminate that forms the elasticized ear flaps 30. Thus, the topsheet 24 of this embodiment should be elongatable, preferably drawable, but not necessarily elastomeric, so that the topsheet 24 will, upon mechanical stretching, be at least to a degree permanently elongated such that it will not fully return to its original configuration. However, this embodiment is not preferred because urine may "wick" beyond the central region 68 of the chassis 14 and fail to be contained within the absorbent assembly.

Figure 8:
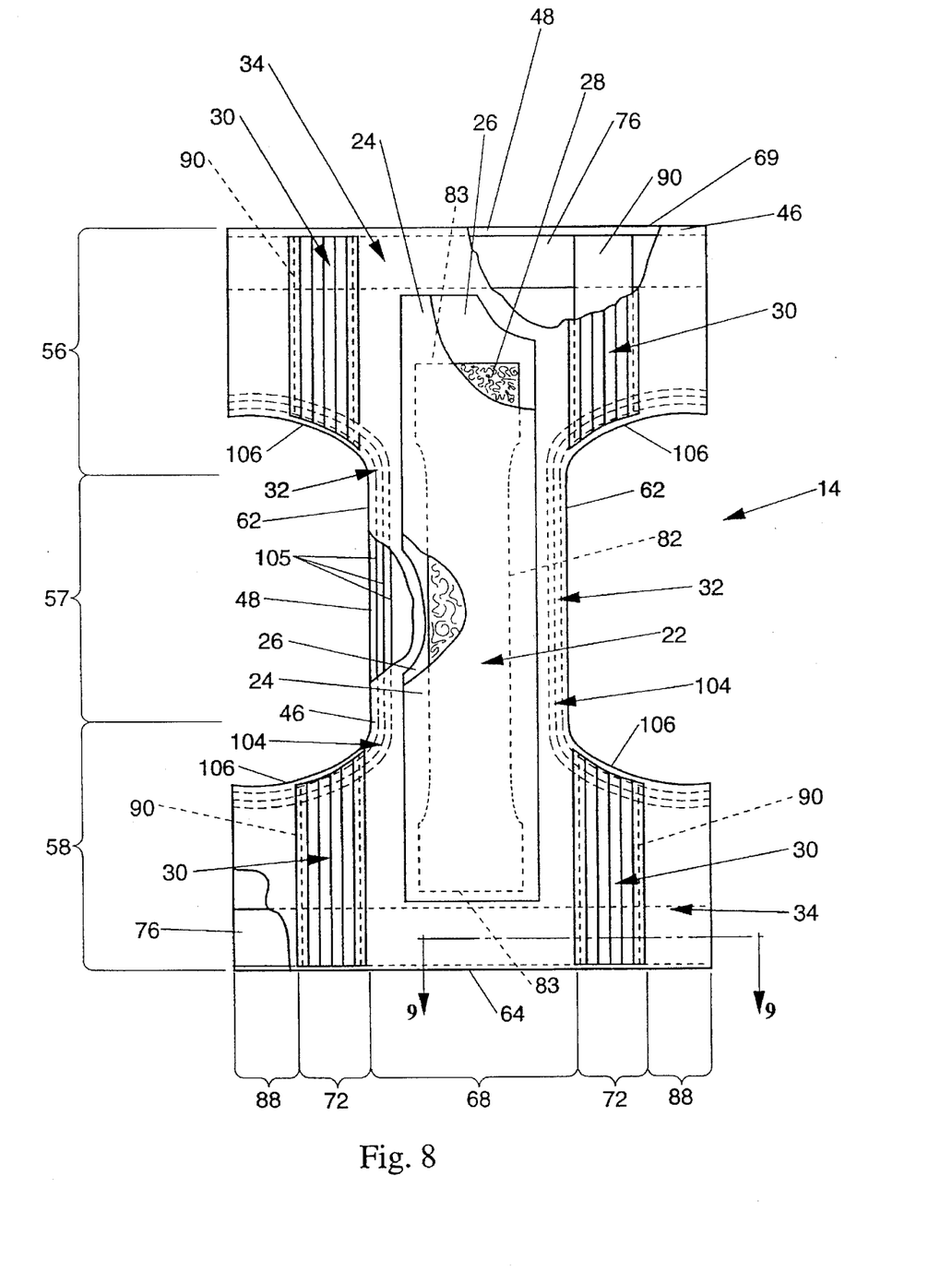
FIG. 8 is a plan view of the laid out training pants of FIG. 7 having portions cut away to reveal the underlying structure.
Figure 9:
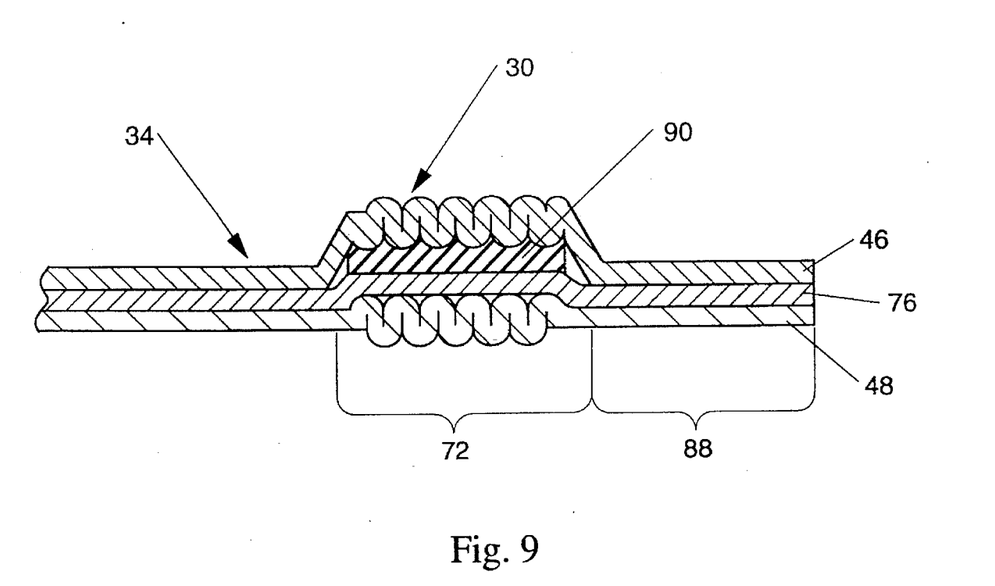
FIG. 9 is a fragmentary sectional view of the chassis shown in FIG. 8 along section line 9—9.

FIG. 7 shows an alternative embodiment of the Hasse training pants 20 having an elastic band disposed throughout the entire length of the waistband and the entire length of the leg bands which overlaps the elasticized ear flaps 30. FIG. 7 and FIG. 8 show a continuous elastic waistband 34 extending between side seams 10 in both the front portion 56 and the rear portion 58, rather than between ear flaps 72 as shown in the first embodiment. The continuous elastic waistband 34 provides a more secure and comfortable fit for the wearer, and permits the training pants 20 to accommodate a broader range of wearers. FIG. 9 shows the area of overlap of the elastic band 76 and the elastic ear flap member 90. Since the elastic will not interfere with or hinder the separability of the non-perforated tear lines, the disposable training pants of the present invention may be constructed with elastic disposed throughout the entire waistband surrounding the waist of the wearer. This embodiment is the preferred embodiment of the invention in terms of providing the best fitting and the best functioning product; however, it is more expensive to produce than the embodiment depicted in FIG. 2 and FIG. 3. Elastic waistbands described in the prior art disclosed opening means that were unable to separate the elastic members of the waistband and leg bands; however, the present invention is capable of severing elastic in waistbands, leg bands and ear flaps.

The alternative embodiment preferably has continous elastic leg bands 32 surrounding the entire leg opening for providing a better fitting training pant with less leakage. Thus, there are portions of overlapping elastic where the elastic leg band 32 overlaps the elasticized ear flap 30. The prior art taught it was preferable to have elastic throughout the entire leg bands, but due to interference with the opening means, only a portion of the leg bands could contain elastic members. Because the present invention permits separation of elasticized portions, the preferred embodiment of the present invention discloses elastic throughout the entire length of the leg bands to facilitate a closer fit around the wearer's legs for enhanced leakage prevention.

It should be understood that the foregoing description and illustrations are by way of example only and such modifications and changes as may suggest themselves to those skilled in the art are intended to fall within the scope of the present invention as defined by the claims.

What is claimed is:

1. An easily removable elasticized disposable undergarment, comprising:

a chassis having a front portion and a rear portion, said front portion and said rear portion contiguous through a crotch portion;

an elastic band located in said chassis;

at least one tear line comprising a series of periodically spaced bond sites separated by unbonded areas located on said chassis and said elastic band, said periodically spaced bond sites providing a zone of weakness such that said chassis tears at said tear line during removal of said undergarment.

2. The undergarment of claim 1 wherein each said bond site is formed by displacing a portion of said chassis to form a thickened outer edge defining an area of reduced thickness.

3. The undergarment of claim 2 wherein approximately 50% to 90% of said portion of said chassis is displaced to said outer edge.

4. The undergarment of claim 3 wherein said bond sites are formed by rotary pressure bonding.

5. The undergarment of claim 3 wherein said bond sites are formed by ultrasonic bonding.

6. The undergarment of claim 3 wherein said tear line is positioned on said front portion of said chassis.

7. The undergarment of claim 1 wherein said elastic band further includes a waistband disposed in at least said rear portion; and legbands disposed in at least said crotch portion.

8. The undergarment of claim 7 wherein said elastic band is elastic film.

9. The undergarment of claim 7 wherein said waistband is further located in said front portion.

10. The undergarment of claim 7 wherein said elastic band is elastic strands.

11. The undergarment of claim 10 wherein adjacent bond sites of said chassis overlap and are spaced such that each elastic strand is overlapped by at least one bond site for severing said elastic strand while retaining said unbonded areas between said bond sites for maintaining strength of said chassis.

* * * * *